(12) United States Patent
Ben Chaabane et al.

(10) Patent No.: US 9,249,402 B2
(45) Date of Patent: Feb. 2, 2016

(54) PROCESS FOR THE CONTINUOUS PRODUCTION OF CELLULASES BY A FILAMENTOUS FUNGUS USING A CARBON SUBSTRATE OBTAINED FROM AN ACID PRETREATMENT

(71) Applicant: IFP ENERGIES NOUVELLES, Rueil-Malmaison Cedex (FR)

(72) Inventors: Fadhel Ben Chaabane, Paris (FR); Bernard Chaussepied, Hanches (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 14/350,827

(22) PCT Filed: Sep. 26, 2012

(86) PCT No.: PCT/FR2012/000381
§ 371 (c)(1),
(2) Date: Apr. 10, 2014

(87) PCT Pub. No.: WO2013/054005
PCT Pub. Date: Apr. 18, 2013

(65) Prior Publication Data
US 2014/0295524 A1 Oct. 2, 2014

(30) Foreign Application Priority Data
Oct. 14, 2011 (FR) ..................... 11 03149

(51) Int. Cl.
| | | |
|---|---|---|
| *C12N 9/42* | (2006.01) | |
| *C12P 21/00* | (2006.01) | |
| *C12N 1/14* | (2006.01) | |
| *C12N 1/38* | (2006.01) | |
| *C12N 9/18* | (2006.01) | |

(52) U.S. Cl.
CPC ................ *C12N 9/2437* (2013.01); *C12N 1/14* (2013.01); *C12N 1/38* (2013.01); *C12N 9/18* (2013.01); *C12P 21/00* (2013.01); *C12Y 301/01073* (2013.01); *Y02E 50/16* (2013.01)

(58) Field of Classification Search
None
See application file for complete search history.

(56) References Cited

U.S. PATENT DOCUMENTS

| 8,093,019 B2 | 1/2012 | Edwards et al. |
| 2009/0061486 A1 | 3/2009 | Edwards et al. |
| 2013/0210119 A1 | 8/2013 | Ben Chaabane et al. |

FOREIGN PATENT DOCUMENTS

| WO | 2009026716 A1 | 3/2009 |
| WO | 2012007650 A1 | 1/2012 |

OTHER PUBLICATIONS

International Search Report from PCT/FR2012/000381 dated Jan. 4, 2013.
Preliminary Search Report and Written Opinion related to Priority Application No. FR1103149 dated Jul. 12, 2012.
Hairong Xiong et al. "Xylanase production by Trichoderma reesei Rut C-30 grown on L-arabinose-rich plant hydrolysates" Bioresource Technology, [2005], vol. 96, pp. 753-759.
D.W. Schafner et al. "Cellulase Production in Continuous Culture by Trichoderma reesei on Xylose-Based Media" Biotechnology and Bioengineering, [1992], vol. 39, pp. 865-869.
Ingrid Persson et al. "Fungal Cellulolytic Enzyme Production: A Review" Process Biochemistry, [1991], vol. 26, pp. 65-74.
Lu-Kwang Ju et al. "Wastepaper Hydrolysate as Soluble Inducing Substrate for Cellulase Production in Continuous Culture of Trichoderma reesei" Biotechnol. Prog. [1999], vol. 15, pp. 91-97.
Tiina M. Pakula et al. "The effect of specific growth rate on protein synthesis and secretion in the filamentous fungus Trichoderma reesei" Microbiology, [2005], vol. 151, pp. 135-143.
Chi-Ming Lo et al. "Cellulase production by continuous culture of Trichoderma reesei Rut C30 using acid hydrolysate prepared to retain more oligosaccharides for induction" Bioresource Technology, [2010], vol. 101, pp. 717-723.
Neil A. Hendy et al. "Enhanced cellulase production in fed-batch culture of Trichoderma reesei C30" Enzyme Microb. Technol., [1984], vol. 6, pp. 73-77.
B.K. Chaudhuri et al. "Comparison of growth and maintenance parameters for cellulase biosynthesis by Trichoderma reesei-C5 with some published data" Enzyme Microb. Technol., [1994], vol. 16, pp. 1079-1083.
D. Ryu et al. "Studies on Quantitative Physiology of Trichoderma-reesei with 2 stage continuous culture for cellulase production" [1979], vol. 21, No. 11, pp. 1887-1904.

*Primary Examiner* — Suzanne M Noakes
(74) *Attorney, Agent, or Firm* — Millen White Zelano and Branigan, PC; Csaba Henter; Anthony Zelano

(57) ABSTRACT

A process for the production of cellulases and hemicellulases using a strain of a filamentous fungus in a stirred and aerated bioreactor, in at least two phases, a phase a) for growth of said strain in the presence of at least one carbonaceous growth substrate in a closed reactor, a phase b) for the continuous production of cellulases, in which at least one carbonaceous inducer substrate is supplied at a supply rate which is constant over a period of at least more than 200 h, said carbonaceous substrate being at least one aqueous hemicellulosic hydrolysate solution obtained from an acid pre-treatment of a lignocellulosic substrate, said aqueous hemicellulosic hydrolysate solution not undergoing prior sterilization and not undergoing pH rectification, being operated at a dilution rate in the range 0.001 to 0.02 $h^{-1}$.

15 Claims, 2 Drawing Sheets

PROCESS FOR THE CONTINUOUS PRODUCTION OF CELLULASES BY A FILAMENTOUS FUNGUS USING A CARBON SUBSTRATE OBTAINED FROM AN ACID PRETREATMENT

FIELD OF THE INVENTION

The present invention relates to the production of cellulases and hemicellulases, in particular in the context of the production of ethanol from lignocellulosic materials. In particular, the present invention relates to a process for the continuous production of cellulase starting from a filamentous fungus.

PRIOR ART

The development of economically viable processes for the production of second generation biofuels is currently a "hot topic". These fuels are produced from lignocellulosic biomass and give rise to fewer problems as regards competition with the use of agricultural land for food compared with "first generation" biofuels which are produced from sugar cane, corn, wheat or beet.

Lignocellulosic biomass is characterized by a complex structure constituted by three principal fractions: cellulose, hemicellulose and lignins. The conventional process for transforming it into ethanol comprises a number of steps. A pre-treatment can render the cellulose accessible to enzymes, namely cellulases. The enzymatic hydrolysis step can be used to transform cellulose into glucose which is then transformed into ethanol during the fermentation step, generally using the yeast Saccharomyces cerevisiae. Finally, a distillation step can separate and recover the ethanol from the fermentation must.

Various technico-economic studies have demonstrated that reducing the cost of cellulases is one of the key points in biological ethanol production processes starting from lignocellulosic substances. Currently, industrial cellulases are principally produced by a filamentous fungus, Trichoderma reesei, because of its high cellulase-secreting power.

Trichoderma reesei is the microorganism which is the most widely used for the production of cellulases. Wild type strains have the ability of excreting cellulose, for example, in the presence of an inducer substrate, the enzymatic cocktail under consideration being the most suitable for hydrolysis of cellulose. The enzymes of the enzymatic cocktail contain three main activity types: endoglucanases, exoglucanases and cellobiases. Other proteins with properties which are vital to hydrolysis of lignocellulosic materials are also produced by Trichoderma reesei, for example xylanases. The presence of an inducer substrate is vital to the expression of cellulolytic and/or hemicellulolytic enzymes.

Regulation of the genes for cellulases on various carbon sources has been studied in detail. They were induced in the presence of cellulose, its hydrolysis products (for example: cellobiose) or certain oligosaccharides such as lactose or sophorose (Ilmén et al, 1997; Appl Environ Microbiol 63: 1298-1306).

Conventional mutational genetic techniques have enabled strains of Trichoderma reesei to be selected which hyperproduce cellulases, such as the strains MCG77 (Gallo—U.S. Pat. No. 4,275,167), MCG 80 (Allen, A. L. and Andreotti, R. E., Biotechnol—Bioengi 1982, 12, 451-459 1982), RUT C30 (Montenecourt, B. S. and Eveleigh, D. E., Appl Environ Microbiol 1977, 34, 777-782) and CL847 (Durand et al, 1984, Proc Colloque SFM "Génétique des microorganismes industriels" [Genetics of industrial microorganisms]. Paris. H. HESLOT Ed, pp 39-50).

The process for the production of cellulases by Trichoderma reesei has been the subject of a great deal of improvement with a view to industrial scale-up. The strategy which is applied industrially is to bring about rapid growth of the fungus to a given concentration in a step known as the growth phase of said fungus, then to induce the production of cellulases starting from said fungus in order to maximize the productivity and yield in a step known as the production phase. Said growth phase is generally carried out in a closed reactor, i.e. in batch mode. Said production phase is generally carried out in a continuously fed reactor during which nothing is withdrawn from the reactor contents, i.e. it is in fed batch mode.

In order to obtain good productivity of the enzymes, it is necessary to provide a source of carbon which can be rapidly assimilated for the Trichoderma reesei to grow in the growth phase, and an inducer substrate which allows the expression of the cellulases and the secretion in the culture medium in the production phase. The cellulose may play a dual role; however, it is difficult to use on an industrial scale and has been replaced by soluble carbon sources such as lactose, which can be used for the expression of cellulases. Other soluble sugars such as cellobiose and sophorose have been described as inducer substrates, but they are too expensive to be used on an industrial scale. However the cellulase production by Trichoderma reesei with soluble substrates is far inferior to that obtained on cellulose in batch mode. This is due to the repressor effect of the sugars that can be readily assimilated at high concentrations.

Continuous supply of soluble carbonaceous inducer substrates in fed batch mode has meant that catabolic repression has been able to be lifted by limiting the residual concentration of carbonaceous substrate in the cultures and by optimizing the quantity of sugar in order to obtain a better yield and better enzymatic productivity. As an example, patent FR-B-2 881 753 describes a process for the production of cellulases comprising two steps:

- a growth phase in "batch" mode where it is necessary to supply a source of carbon that can be rapidly assimilated for growth of Trichoderma reesei, then
- a "fed batch" production phase using an inducer substrate such as lactose, for example, which allows the expression of cellulases and the secretion into the culture medium. The soluble carbonaceous substrate is supplied continuously at a specific optimized flow rate, expressed in mg of substrate per gram of the dry weight of filamentous fungus per hour, in the range 35 to 45 $mg \cdot g^{-1} \cdot h^{-1}$.

In that patent, the protein production step is not carried out beyond approximately 170 h. That protocol means that a concentration of proteins of the order of 35 to 40 g/L can be obtained with a productivity of the order of 0.2 g/L/h.

However, the reactor has to be cleaned and a new seeding sequence has to be carried out. The disadvantage of this mode of operation is too low a productivity, which means that the initial investment in the number of enzyme production fermenters has to be increased. The protein concentration obtained is also low, and frequently a concentration step is required after filtration of the mycelium. All of this contributes to making the second generation ethanol production process lack in competitiveness.

One aim of the present invention is to provide a process for the production of cellulases and hemicellulases using at least one specific carbonaceous inducer substrate obtained from acid pre-treatment of a lignocellulosic substrate in order to increase or even double the productivity and concentration of cellulases and hemicellulases produced compared with prior art processes, and to produce these cellulases continuously over an increased period. The process of the present invention can be used to increase or even double the productivity and concentration of the cellulases and hemicellulases produced while maintaining the cellulase production yield constant compared with the carbonaceous substrate used in prior art processes.

SUMMARY AND ADVANTAGE OF THE INVENTION

The present invention concerns a process for the production of cellulases and hemicellulases using a strain of a filamentous fungus in a stirred and aerated bioreactor, comprising at least two phases:
- a phase a) for growth of said strain in the presence of at least one carbonaceous growth substrate in a closed reactor, said growth phase being carried out with a concentration of carbonaceous growth substrate in the range 10 to 90 g/L;
- a phase b) for the continuous production of cellulases, in which at least one carbonaceous inducer substrate is supplied at a supply rate which is constant over a period of at least more than 200 h, said carbonaceous inducer substrate being at least one aqueous hemicellulosic hydrolysate solution obtained from an acid pre-treatment of a lignocellulosic substrate, said aqueous hemicellulosic hydrolysate solution not undergoing prior sterilization and not undergoing pH rectification, said pH of the aqueous solution being in the range 0.5 to 3, the mass of the reaction volume being kept constant by withdrawing a fraction of said reaction volume, said phase b) being operated at a dilution rate in the range 0.001 to 0.02 $h^{-1}$.

Advantage of the invention

One advantage of the present invention is that it can be used to improve the productivity and concentration of proteins produced over an increased operational period. In particular, the process of the invention can be used to obtain a concentration of proteins of more than 100 g/L. These performances have been maintained experimentally in continuous mode for more than 400 h.

The high productivity obtained means that bioreactor investment costs can be reduced. The prolonged period means that the time devoted to cleaning the bioreactors and the seeding sequences can be reduced. The high concentration of cellulases means that post-treatment costs can be reduced.

Another advantage of the continuous process of the invention is that it necessitates a low $k_La$ both because of the application of a low dilution rate in continuous production phase b) and the use of a specific carbonaceous inducer substrate solution in said phase b), which means that the viscosity in the reaction medium can be kept low.

DETAILED DESCRIPTION OF THE INVENTION

Figure 1:
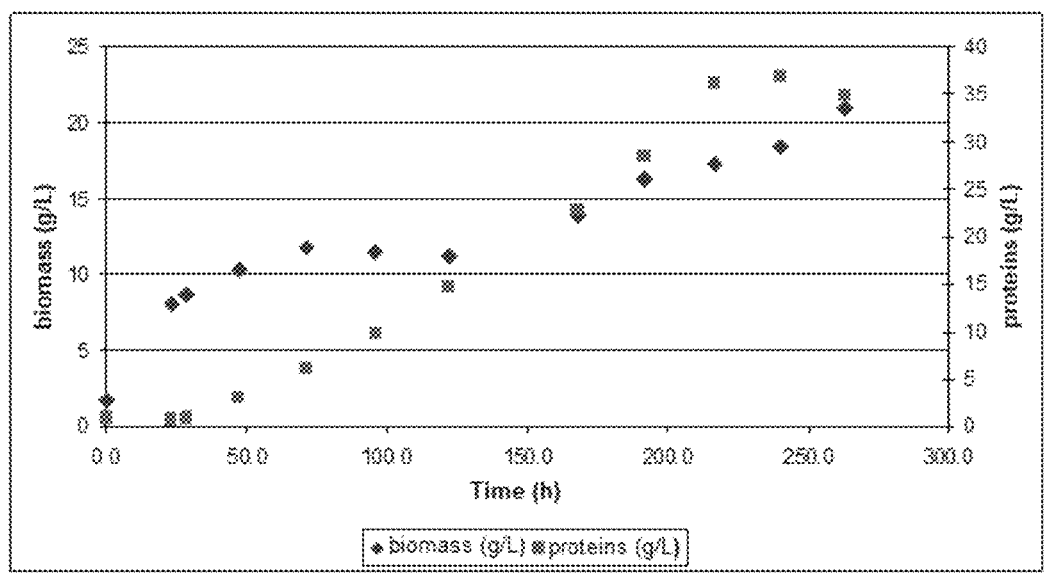
FIG. 1—Shows the change in the concentration of biomass and proteins (g/L).

The process of the invention is preferably operated at a pH in the range 3 to 6, at a temperature in the range 20° C. to 35° C., at a vvm, i.e. a degree of aeration expressed as the volume of air under normal temperature and pressure conditions per volume of reaction medium per minute, in the range 0.3 to 1.5 $min^{-1}$, preferably in the range 0.3 to 1 $min^{-1}$, and with stirring that can produce a partial pressure of oxygen in the reaction medium in the range 20% to 60%, preferably in the range 20% to 40%.

Preferably, the process of the invention is operated at a vvm of 0.5 $min^{-1}$ and with stirring which means that the partial pressure of oxygen can be set at 30%.

In accordance with the invention, said process comprises a phase a) for growth of the strain of a filamentous fungus, preferably the fungus *Trichoderma reesei*, in the presence of at least one carbonaceous growth substrate in a closed reactor, said growth phase being carried out with a concentration of carbonaceous growth substrate in the range 10 to 90 g/L.

Said strain used in the process of the invention is a strain of a filamentous fungus preferably belonging to the genera *Trichoderma, Aspergillus, Penicillium* or *Schizophyllum*, and preferably said strain belongs to the species *Trichoderma reesei*.

The strain used preferably from the species *Trichoderma reesei* may advantageously be modified by mutation-selection processes in order to improve the cellulolytic and/or hemicellulolytic enzymes such as, for example, the strain IFP CL847. A strain improved by genetic recombination techniques may also be used. Said strain is cultured in stirred, aerated reactors under conditions which are compatible with its growth and with cellulase production. Other microorganism strains producing cellulases using processes similar to those used for *Trichoderma* may be used.

Highly preferably, the strain used is a strain of *Trichoderma reesei* modified by genetic mutation, selection or recombination.

The strain may advantageously be selected from the strains CL847, RutC30, MCG77, or MCG80.

The carbonaceous growth substrate used in said growth phase is advantageously selected from soluble industrial sugars, and preferably from glucose, lactose, xylose, residues obtained after ethanolic fermentation of the monomeric sugars of enzymatic hydrolysates of the lignocellulosic substrate and extracts of the hemicellulosic fraction in the form of monomers deriving from the pre-treated lignocellulosic substrate, used alone or as a mixture.

Depending on its nature, said carbonaceous substrate is advantageously introduced into the reactor before sterilizing said reactor, or is sterilized separately and introduced into the pre-sterilized reactor.

Preferably, the concentration of carbonaceous growth substrate is in the range 30 to 70 g/L.

Preferably, the growth phase a) is carried out over a period in the range 30 to 70 h, preferably in the range 40 to 60 h.

Preferably, the growth phase a) is operated at a pH of 4.8 and at a temperature of 27° C.

In accordance with the invention, said process comprises a phase b) for the continuous production of cellulases, in which at least one carbonaceous inducer substrate is supplied at a supply rate which is constant over a period of at least more than 200 h, said carbonaceous substrate being at least one aqueous hemicellulosic hydrolysate solution obtained from an acid pre-treatment of a lignocellulosic substrate, said aqueous hemicellulosic hydrolysate solution not undergoing prior sterilization and not undergoing pH rectification, said pH of the aqueous solution being in the range 0.5 to 3, the mass of the reaction volume being kept constant by withdrawing a fraction of said reaction volume, said phase b) being operated at a dilution rate in the range 0.001 to 0.02 $h^{-1}$.

Said continuous phase is advantageously carried out in a continuously fed reactor during which a fraction of the reaction volume is withdrawn so as to keep the mass of the reaction volume constant. Said continuous phase is known as the "chemostat" mode.

The lignocellulosic substrate which can be used to obtain the aqueous hemicellulosic hydrolysate solution used in phase b) of the process of the invention is a source of carbon hydrates composed of three principal constituents: cellulose (35% to 50%), hemicelluloses (20% to 30%), which are polysaccharides essentially constituted by pentoses and hexoses, and lignin (15% to 25%), which is a macromolecule with a complex structure and a high molecular weight composed of aromatic alcohols connected via ether bonds. Said substrate is advantageously selected from straw, wood, forest cultures, residues of alcoholigenic sugar and cereal plants, residues from the paper industry and transformation products of lignocellulosic materials.

The acid pre-treatment which the lignocellulosic substrate undergoes is carried out in accordance with acid pre-treatments which are known to the skilled person. Preferably, the acid pre-treatment is an acid hydrolysis, acid cooking or steam explosion with prior impregnation of said lignocellulosic substrate with an aqueous sulphuric acid solution.

The aqueous hemicellulosic hydrolysate solution obtained has a pH in the range 0.5 to 3 and is used with neither a sterilization step nor a pH rectification step.

Preferably, said aqueous hemicellulosic hydrolysate solution has a pH in the range 0.5 to 2.

The carbonaceous inducer substrate used in phase b) of the process of the invention is advantageously an aqueous hemicellulosic hydrolysate solution obtained from an acid pre-treatment of a lignocellulosic substrate, alone or as a mixture with at least one other carbonaceous substrate which has not undergone sterilization.

Preferably, said carbonaceous substrates are selected from inducer or non-inducer sugars, preferably selected from lactose, glucose, cellobiose and xylose, used alone or as a mixture.

Said substrates are dissolved in said aqueous hemicellulosic hydrolysate solution.

In the case in which the carbonaceous inducer substrate is an aqueous hemicellulosic hydrolysate solution obtained from an acid pre-treatment of a lignocellulosic substrate mixed with at least one other carbonaceous substrate which has not undergone sterilization, said carbonaceous inducer substrate has a concentration in the range 200 to 600 g/L depending on the degree of solubility of the carbonaceous substrates used.

In the case in which the carbonaceous inducer substrate is an aqueous hemicellulosic hydrolysate solution obtained from an acid pre-treatment of a lignocellulosic substrate alone, said carbonaceous inducer substrate has a concentration in the range 40 to 400 g/L possibly after having been concentrated.

Using said specific carbonaceous inducer substrate obtained from acid pre-treatment of a lignocellulosic substrate means that phase b) for the production of cellulases can be carried out for an increased period compared with the prior art process, preferably for more than 200 h.

In accordance with the invention, said carbonaceous inducer substrate is supplied at a supply flow rate which is at least constant. Preferably, the supply flow rate for said carbonaceous inducer substrate is in the range 35 to 140, preferably in the range 35 to 60 mg of carbonaceous inducer substrate per gram of dry strain per hour.

Preferably, the supply flow rate is gradually increased in phase b), more preferably gradually increased until it is doubled in the first operational hours of phase b), preferably after at least 24 h and more preferably after at least 48 h of operating phase b).

In accordance with the invention, the duration of phase b) for the continuous production of cellulases is at least more than 200 h, preferably at least more than 300 h and more preferably at least more than 400 h.

In phase b), the mass of the reaction volume is kept constant by withdrawing a fraction of said reaction volume.

Preferably, withdrawal is carried out using withdrawal methods which are known to the skilled person such as, for example, by means of a regulating system and a programmable drainage pump.

Preferably, the withdrawal rate is at least equal to the supply rate into phase b).

In accordance with the invention, the dilution rate, defined as the ratio of the withdrawal flow rate to the reaction volume of the reactor during continuous production phase b), is advantageously in the range 0.001 $h^{-1}$ to 0.02 $h^{-1}$, preferably in the range 0.002 to 0.008 $h^{-1}$. The highly preferred dilution rate is 0.004 $h^{-1}$.

Preferably, phase b) is operated at a pH in the range 3 to 5.5 and at a temperature in the range 20° C. to 30° C.

An optional production phase a') carried out in a reactor with a continuous supply of at least one carbonaceous inducer substrate during which no withdrawal of the contents of the fermenter is carried out, i.e. in fed batch mode, is advantageously carried out between phase a) and phase b).

Carrying out said phase a') means that the fraction of reaction volume containing the filamentous fungus strain is not withdrawn while the concentrations of the proteins produced are still low.

Said carbonaceous inducer substrate used in phase a') is identical to the carbonaceous inducer substrate used in the production phase b).

Preferably, the supply flow rate for said carbonaceous inducer substrate is in the range 35 to 140, preferably in the range 35 to 60 mg of carbonaceous inducer substrate per gram of dry strain per hour. Said supply flow rate is kept constant throughout the duration of phase a').

Preferably, phase a') is carried out for a period in the range 50 to 150 h, preferably in the range 70 to 130 h.

Preferably, phase a') is operated at a pH in the range 3 to 5.5 and at a temperature in the range 20° C. to 30° C.

The process of the present invention means that the productivity can be increased or even doubled, along with the concentration of cellulases and hemicellulases produced compared with prior art processes, and these cellulases can be continuously produced for a longer period.

EXAMPLES

Example 1

Not in Accordance

Example 1 presents a culture using the reference conditions of patent FR-B-2 881 753. Example 1 illustrates a process for the production of cellulases and hemicellulases comprising a growth phase and a production phase in fed batch mode carried out for 167 h.

Production of cellulases and hemicellulases was carried out in a mechanically stirred 3 L reactor. The mineral medium had the following composition: KOH 1.66 g/L, 85% $H_3PO_4$ 2 mL/L, $(NH_4)_2SO_4$ 2.8 g/L, $MgSO_4 \cdot 7 H_2O$ 0.6 g/L, $CaCl_2$ 0.6 g/L, $MnSO_4$ 3.2 mg/L, $ZnSO_4 \cdot 7 H_2O$ 2.8 mg/L, $CoCl_2$ 10 4.0 mg/L, $FeSO_4 \cdot 7 H_2O$ 10 mg/L, Corn Steep 1.2 g/L, anti-foaming agent 0.5 mL/L.

A liquid pre-culture of the *Trichoderma reesei* CL847 strain was produced. The mineral medium of the pre-culture was identical to that of the reactor apart from adding 5 g/L potassium phthalate to buffer the pH. Growth of the fungus in pre-culture was carried out using glucose as the carbonaceous substrate at a concentration of 30 g/L. Growth of the inoculum lasted 2 to 3 days and was carried out at 28° C. in a stirred incubator at atmospheric pressure.

The reactor containing the mineral medium was sterilized at 120° C. for 20 minutes; the glucose carbonaceous substrate was sterilized from 120° C. for 20 minutes then added to the reactor in a sterile manner in order to produce a final concentration of 30 g/L. The reactor was seeded to 10% (v/v) with said liquid pre-culture of the *Trichoderma reesei* CL847 strain as soon as the residual glucose concentration in the pre-culture was less than 15 g/L.

The experiment carried out in the bioreactor comprised two phases:
- a phase for growth on a carbonaceous glucose substrate (initial concentration=30 g/L) at a temperature of 27° C. and a pH of 4.8 (set using a 5.5 M ammoniacal solution). Aeration was at 0.5 vvm and stirring was increased to between 200 and 800 rpm as a function of the $pO_2$ (pressure of dissolved oxygen), which was set at 30%.
- a protein production phase in fed batch mode. After 30 hours, a 250 g/L carbonaceous lactose solution was continuously injected at a flow rate of 4 mL/h, i.e. at 35 mg of lactose per g of *Trichoderma reesei* CL847 strain per hour, up to 167 hours. The temperature was dropped to 25° C. and the pH to 4 until culture had ended. The pH was set by adding a 5.5 M ammoniacal solution which provided the nitrogen necessary for the synthesis of the excreted cellulases and hemicellulases. The quantity of dissolved oxygen was kept above 30% by the stirring action.

Cellulase production was followed by assaying the extracellular proteins using Lowry's method and standard BSA, after separating the mycelium by filtering or centrifuging. The cellulolytic activities determined were:
- the filter paper activity (FPU: filter paper unit) which could be used to assay the overall activity of the enzymatic endoglucanases and exoglucanases pool;
- the β-glucosidase activity for the specific activities.

The FPU activity was measured on Whatman N° 1 paper using the procedure recommended by the IUPAC biotechnological commission at an initial concentration of 50 g/L; the test sample of the enzymatic solution to be analysed which liberated the equivalent of 2 g/L of glucose (colorimetric assay) in 60 minutes was determined. The principle of filter paper activity is to determine, by dinitrosalicylic acid (DNS) assay, the quantity of reduced sugars obtained from a Whatman N° 1 paper.

The substrate used to determine the β-glucosidase activity was p-nitrophenyl-β-D-glucopyranoside (PNPG). It is cleaved by β-glucosidase, which liberates p-nitrophenol.

One β-glucosidase activity unit is defined as the quantity of enzyme necessary to produce 1 μmole of p-nitrophenol from PNPG per minute and is expressed in IU/mL.

The specific activities were obtained by dividing the activities, expressed in IU/mL, by the cellulase concentration. They were expressed in IU/mg.

The final productivity was calculated using the whole mass of the cellulases and hemicellulases produced during the production phase (including samples) and dividing it by the duration of the production phase and the useful volume of the reactor.

The term "biomass" characterizes the *Trichoderma reesei* CL847 strain.

The term "protein" is defined as being the enzymatic cocktail obtained comprising the cellulases and hemicellulases produced.

The analytical determinations on the final must of Example 1 produced the following results:
Biomass, g/L=14.4
Proteins, g/L=35.7
Productivity=0.21 g/L/h
FPU=22.1 IU/mL
Specific β-glucosidase=0.8 IU/mg

Example 2

Not in Accordance

Example 2 presents a culture analogous to that of Example 1, except that the fed batch mode was continued beyond 200 h with the same supply substrate. It was observed that the production of cellulases and hemicellulases stopped after 200 h. They actually started to degrade, since the concentration dropped from 37 g/L to 35 g/L. The biomass itself increased during this period to reach a concentration of 20.9 g/L. Assays showed that sulphur was deficient.

The change in the concentration of biomass and proteins (g/L) is shown in FIG. 1.

The analytical determinations on the final must produced the following results:
Biomass, g/L=20.9
Proteins, g/L=35.1
Productivity=0.13 g/L/h (it was 0.17 g/L/h after 216 h)
FPU=16.1 IU/mL
Specific β-glucosidase=0.7 IU/mg

Example 3

In Accordance with the Invention

Example 3 was initiated under the same conditions as those for Example 1, but comprised 3 phases:
- a phase a) in batch mode under the same conditions as those for Example 1, but with a glucose concentration of 60 g/L. This phase lasted 50 h;
- a second phase a') in fed batch mode. The fed batch was initiated as soon as the carbonaceous glucose substrate was exhausted with a hemicellulosic hydrolysate solution obtained from straw pre-treated by steam explosion with prior impregnation of $H_2SO_4$ in which glucose and lactose had been dissolved in order to obtain an overall concentration of carbonaceous substrate of 500 g/L. This solution was not sterilized and its pH was not raised and was equal to 1. A flow rate of 4 mL/h (i.e. a flow of 35 mg of sugars per g of *Trichoderma reesei* CL847 strain per hour) was applied. This phase lasted 100 h;

a phase b) for the continuous production of cellulases and hemicellulases was then initiated. The supply flow rate was kept constant at 4 mL/h throughout the experiment. The reactor was maintained at a constant weight by continuously withdrawing the must using a regulating system and with a programmable pump. The dilution rate was $0.002\ h^{-1}$.

After 400 h, we continuously produced an enzymatic solution having a concentration of more than 100 g/L and with a productivity of more than 0.2 g/L/h.

This therefore meant that the concentration of proteins had trebled and the productivity was higher than that of Example 1 (+20%).

Figure 2:
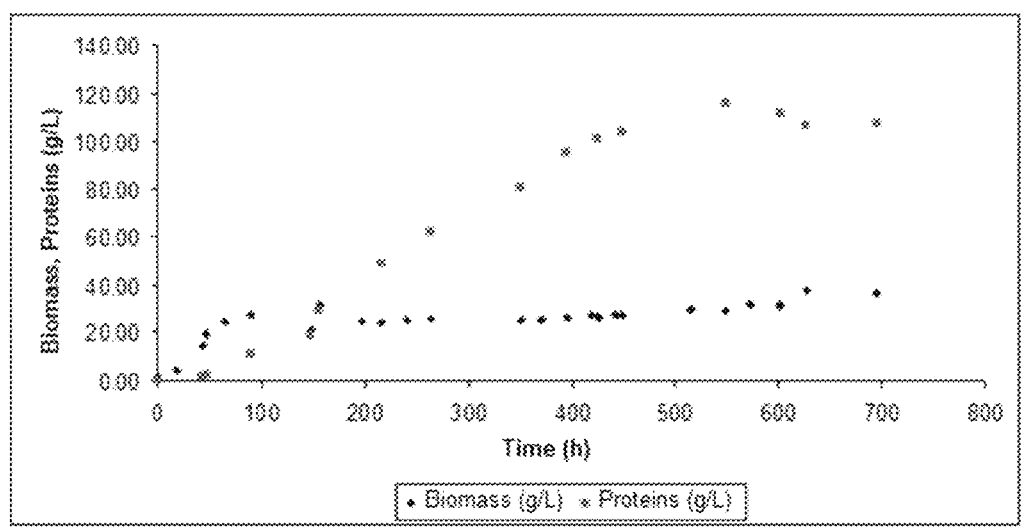
FIG. 2—Shows the change in the concentration of biomass and proteins (g/L) with time for Example 3.

The change in the concentration of biomass and proteins (g/L) with time for Example 3 in which the continuous phase was initiated after 150 h with a flow rate of 4 mL/h is shown in FIG. 2.

The analytical determinations on the final must produced the following results:
Biomass, g/L=36.7
Proteins, g/L=107.2
Final productivity=0.26 g/L/h
FPU=76.8 IU/mL
Specific β-glucosidase=1.2 IU/mg Example 4

In Accordance

Example 4 was analogous to Example 3, with the exception that the continuous production phase was initiated directly after the batch mode growth phase a) and that the supply flow rate of carbonaceous inducer substrate in the continuous production phase b) was gradually increased from 4 mL/h to 8 mL/h, i.e. increased by 1 mL every 12 h after launching said phase b). The carbonaceous inducer substrate used was the same as that in example 3, i.e. a solution of hemicellulose hydrolysate obtained from straw pre-treated by steam explosion with prior impregnation of $H_2SO_4$ in which glucose and lactose had been dissolved. This solution was not sterilized and its pH was not raised and was equal to 1. The operating conditions used in phases a) and b) were identical to those used in Example 3. When the increase in the supply flow rate of carbonaceous inducer substrate was complete, the dilution ratio was $0.004\ h^{-1}$. The mass of the reaction volume was kept constant.

The final productivity of the experiment was 0.39 g/L/h. It was almost double that of Example 1. This meant that investment costs could be reduced. The final protein concentration was almost trebled. This meant that post-treatment costs could be reduced, in particular, if appropriate, the concentration of proteins produced. The culture did not require a high $k_L a$ (approximately $75\ h^{-1}$) because of the low dilution ratio applied, which thus meant that operating costs linked to stirring and aeration were low.

Figure 3:
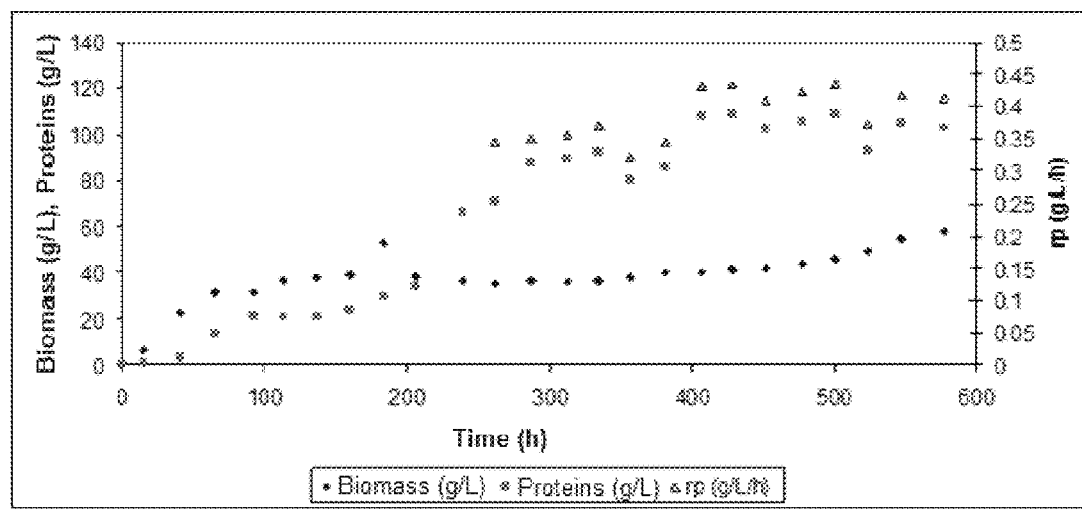
FIG. 3—Shows the change in productivity (rp) of cellulases and the concentrations of *T. reesei* strains and cellulases for Example 4.

The change in productivity (rp) of cellulases and the concentrations of T. reesei strains and cellulases for Example 4 in which the continuous phase was initiated after 150 h and the fed batch flow rate was increased from 4 to 8 mL/h is shown in FIG. 3.

The analytical determinations on the final must produced the following results:
Biomass, g/L=58.1
Proteins, g/L=102.9
Final productivity=0.39 g/L/h
FPU=77.6 IU/mL
Specific β-glucosidase=1.3 IU/mg The productivity was almost double that of Example 1 and the concentration of proteins was almost trebled. Said concentration was maintained for more than 300 h.

Example 5

Not in Accordance

Example 5 was able to show the effect of not sterilizing the hemicellulosic hydrolysate solution obtained from straw pre-treated by steam explosion with prior impregnation of $H_2SO_4$ on the performance of the process.

Example 5 was initiated under the same conditions as Example 4, with the exception that the hydrolysate solution was sterilized before use. The concentration of said solution was 250 g/L. The culture resulted in a strong accumulation of the T. reesei strain and a low production of cellulases. The oxygen demand was very high at the end of culture, with a necessary $k_L a$ of more than $170\ h^{-1}$.

The protein production yield compared with the carbonaceous substrate was less than 0.1 g/g, while it was 0.3 g/g for Examples 1 to 4.

The analytical determinations on the final must produced the following results:
Biomass, g/L=99.8
Proteins, g/L=24.2
FPU=14.5 IU/mL
Specific β-glucosidase=1.1 IU/mg Example 6

Not in Accordance

Example 6 demonstrates the disadvantage of operating in continuous phase at a high dilution rate which resulted in a viscous medium and in problems with clogging of the drainage pump due to the morphology of the fungus when it was in the growth phase. The $k_L a$ and thus the operating costs linked to stirring and aeration of the medium were high.

Example 6 was carried out under the same conditions as Example 4, with a first phase a) for growth in batch mode which lasted 50 h and a continuous phase b) for the production of cellulases and hemicellulases. The solution which supplied the production phase was a hemicellulosic hydrolysate solution which had not been sterilized into which lactose had been dissolved to a concentration of 250 g/L. The supply flow rate for the carbonaceous inducer substrate was 13 mL/h, which corresponded to 54 mg of sugars per g of Trichoderma reesei CL847 strain per hour. The mass of the reaction volume was kept constant and the dilution rate which was applied was $0.025\ h^{-1}$.

The experiment was very difficult to carry out, with repeated clogging of the drainage pump, because the medium was very viscous when the fungus was growing. Fungus production was high and the $pO_2$ index value could not be maintained above 0%. A stationary state could not be reached. The $k_L a$ of the bioreactor was not sufficient to supply the necessary oxygen, meaning that all of the flux of sugar which was supplied was consumed. $k_L a$ values of $700\ h^{-1}$ were, however, measured over water with this reactor.

Example 7

Not in Accordance

Figure 4:
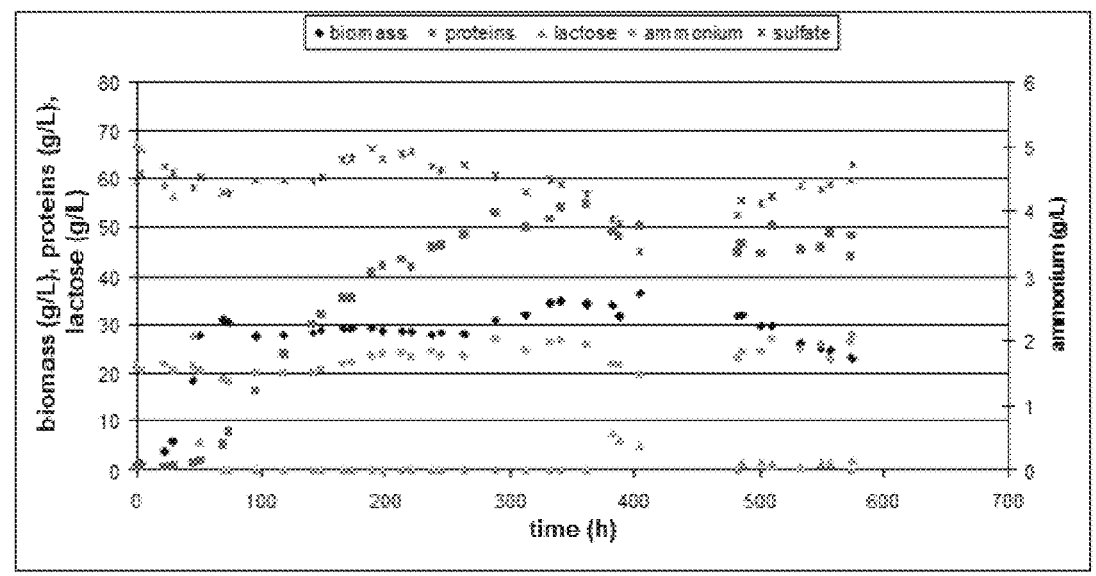
FIG. 4—Shows the changes in the concentrations of cellular biomass and proteins.

Example 7 was carried out under the same conditions as those for Example 3, with the only difference being that the phase in batch mode was carried out with a concentration of glucose of 65 g/L. The phase a') in fed batch mode and the phase b) for production in continuous mode were carried out under the same conditions, with the only difference being that the solution which supplied phases a') and b) was a 250 g/L lactose solution acidified by adding sulphuric acid, $H_2SO_4$, such that said solution had a pH of 1.5. The changes in the concentrations of cellular biomass and proteins are shown in FIG. 4. FIG. 4 also shows the change in the concentrations of sulphates and ammonium ions which were non-limiting. The experiment was not able to obtain a conversion of proteins of more than 50 g/L. The concentration of proteins stabilized at 50 g/L after 400 hours.

The results obtained demonstrate the importance of using a solution of hemicellulosic hydrolysates in the continuous production phase and that the performances obtained were not due to overcoming the deficiency of sulphur and nitrogen.

The analytical determinations on the final must produced the following results:
Biomass, g/L=23
Proteins, g/L=48.3
FPU=31.2
Specific β-glucosidase=1.1

Example 8

Not in Accordance

Example 8 was carried out under the same conditions as for Example 3, with the only exception being that the hemicellulosic hydrolysate solution obtained from straw pre-treated by steam explosion with prior impregnation with $H_2SO_4$ into which glucose and lactose had been dissolved was not sterilized but underwent rectification of its pH by adding NaOH. Its pH rose to 4.

Protein production did not stop after 160 h and remained stable at a concentration of close to 20 g/L.

The analytical determinations on the final must produced the following results:
Biomass, g/L=25.1
Proteins, g/L=19.8
FPU=15.8 IU/mL
Specific β-glucosidase=1.2 IU/mg

The invention claimed is:

1. A process for the production of cellulases and hemicellulases with a strain of a filamentous fungus in a stirred and aerated bioreactor, comprising:
producing cellulases and hemicellulases with a strain of a filamentous fungus in a stirred and aerated bioreactor in at least two phases:
a phase a) for growth of said strain in the presence of at least one carbonaceous growth substrate in a closed reactor, said growth phase being carried out with a concentration of carbonaceous growth substrate of 10 to 90 g/L; and
a phase b) for the continuous production of cellulases, in which at least one carbonaceous inducer substrate is supplied at a supply rate which is constant over a period of at least more than 200 h, said carbonaceous inducer substrate being at least one aqueous hemicellulosic hydrolysate solution obtained from an acid pre-treatment of a lignocellulosic substrate, said aqueous hemicellulosic hydrolysate solution not undergoing prior sterilization and not undergoing pH rectification, said pH of the aqueous solution being 0.5 to 3, the mass of the reaction volume being kept constant by withdrawing a fraction of said reaction volume, said phase b) being operated at a dilution rate of 0.002 to 0.008 $h^{-1}$.

2. The process according to claim 1, in which said strain is a strain of *Trichoderma reesei* modified by mutation, selection or genetic recombination.

3. The process according to claim 1, in which the carbonaceous growth substrate in said growth phase is glucose, lactose, xylose, a residue obtained after ethanolic fermentation of monomeric sugars of an enzymatic hydrolysate of a lignocellulosic substrate, an extract of a hemicellulosic fraction in the form of monomers deriving from a pre-treated lignocellulosic substrate, or a combination thereof.

4. The process according to claim 1, in which the acid pre-treatment is an acid hydrolysis, acid cooking or steam explosion with prior impregnation of said lignocellulosic substrate with an aqueous sulphuric acid solution.

5. The process according to claim 1, in which the carbonaceous inducer substrate in phase b) is an aqueous hemicellulosic hydrolysate solution obtained from an acid pre-treatment of a lignocellulosic substrate, as a mixture with at least one other carbonaceous substrate of inducer or non-inducer sugars.

6. The process according to claim 1, in which the duration of phase b) for the continuous production of cellulases is more than 300 h.

7. The process according to claim 6, in which the duration of phase b) for the continuous production of cellulases is more than 400 h.

8. The process according to claim 1, in which the supply flow rate of said carbonaceous inducer substrate is 35 to 140 mg of carbonaceous inducer substrate per gram of the dry weight of the strain per hour.

9. The process according to claim 1, in which the supply flow rate is gradually increased in phase b).

10. The process according to claim 1, in which an optional phase a') for growth and production in a reactor with a continuous supply of at least one carbonaceous inducer substrate during which no continuous withdrawal from the fermenter occurs, is carried out between phase a) and phase b).

11. The process according to claim 10, in which said carbonaceous inducer substrate in phase a') is identical to the carbonaceous inducer substrate in the production phase b).

12. The process according to claim 10, in which phase a') is carried out for a period of 50 to 150 h.

13. The process according to claim 1, wherein the vvm is 0.3 to 1.5 $min^{-1}$ wherein the vvm is the degree of aeration expressed as the volume of air under normal temperature and pressure conditions per volume of reaction medium per minute.

14. The process according to claim 13, wherein the vvm is 0.3 to 1 $min^{-1}$.

15. The process according to claim 13, wherein the vvm is 0.5.

* * * * *